United States Patent [19]
Himes et al.

[11] Patent Number: 6,152,941
[45] Date of Patent: Nov. 28, 2000

[54] ENDOSCOPIC CANNULATED HANDPIECE MOTOR WITH INTEGRATED SUCTION CONTROL

[75] Inventors: David M. Himes, Los Gatos; Steven A. Tyler, San Francisco; Erik D. Eli, San Jose; Michael V. Madsen, San Jose; Matthew J. Curran, San Jose; Marshal E. Finley, Santa Cruz, all of Calif.

[73] Assignee: Stryker Corporation, Kalamazoo, Mich.

[21] Appl. No.: 09/058,654

[22] Filed: Apr. 10, 1998

[51] Int. Cl.[7] .................................................. A61B 17/14
[52] U.S. Cl. ......................... 606/180; 606/80; 606/167; 604/22
[58] Field of Search ............................... 606/79, 80, 167, 606/159, 166, 170, 179, 180, 185; 604/19, 22, 35

[56] References Cited

U.S. PATENT DOCUMENTS

| | | | |
|---|---|---|---|
| 2,812,765 | 11/1957 | Tofflemire | 604/32 |
| 4,705,038 | 11/1987 | Sjostrom et al. | 606/180 |
| 4,895,146 | 1/1990 | Draenert | 606/180 |
| 5,203,769 | 4/1993 | Clement et al. | 604/32 |
| 5,207,697 | 5/1993 | Carusillo et al. . | |
| 5,520,634 | 5/1996 | Fox et al. | 606/180 |
| 5,569,256 | 10/1996 | Vaughn et al. | 606/180 |
| 5,601,560 | 2/1997 | Del Rio et al. | 606/80 |
| 5,871,493 | 2/1999 | Sjostrom et al. | 606/180 |
| 5,910,152 | 6/1999 | Bays . | |

FOREIGN PATENT DOCUMENTS

97/16124  5/1997  WIPO .

OTHER PUBLICATIONS

Arthrotek Shaver, photographs (8 photographs—4 sheets) Mar., 1998.

*Primary Examiner*—Glenn K. Dawson
*Attorney, Agent, or Firm*—Flynn, Thiel, Boutell & Tanis, P.C.

[57] ABSTRACT

A surgical handpiece includes a housing having an interior cavity and an exterior surface adapted to be gripped by the hand of a user. A rotary drive mechanism is provided inside of the housing and includes a driven shaft with a passageway extending axially therethrough. A suction connection is provided on the housing as is a suction control mechanism operable between first and second operative positions for preventing suction from being applied to the passageway in the driven shaft when in a first operative position and for connecting suction to the passageway when in a second operative position.

11 Claims, 10 Drawing Sheets

ENDOSCOPIC CANNULATED HANDPIECE MOTOR WITH INTEGRATED SUCTION CONTROL

FIELD OF THE INVENTION

This invention relates to a surgical handpiece and, more particularly, to an endoscopic cannulated handpiece motor having an integrated suction control device for controlling suction to a passageway in a shaft driven by the motor.

BACKGROUND OF THE INVENTION

Motorized surgical handpieces are well-known in the art. Such motorized surgical handpieces usually include various kinds of cutting instruments. Some surgical procedures require that the area whereat surgery is occurring to be periodically flushed with a saline solution and a suction apparatus employed to remove the saline solution along with detritus material freed during the cutting procedure. Some surgical procedures employ a surgical opening that is too small for multiple instruments to be present at the surgical site at one time. While saline solution can be conveniently delivered to the area, removal of the saline solution and the detritus material is complicated by the presence of the surgeon's tool in the surgical area. Thus, there exists a need to provide a solution to the aforesaid problem.

Accordingly, it is an object of the invention to provide a surgical handpiece having a motorized driven shaft configured to drive a surgical tool and an integrated suction control mechanism for opening and closing a connection to a suction source so as to, respectively, connect suction to a passageway through the surgical handpiece and tool when in one position and blocking suction to the passageway and tool when in another position.

It is a further object of the invention to provide a surgical handpiece, as aforesaid, which can be conveniently gripped by a single hand of the hand of a user and be easily operable and controlled in a manner suitable to the user.

It is a further object of the invention to provide a surgical handpiece, as aforesaid, wherein the drive mechanism includes in a housing of the surgical handpiece a stator affixed to the housing with a rotor being radially aligned with the stator so that electrical energization of the stator will effect a rotation of the rotor and a hollow driven shaft affiliated with the rotor.

It is a further object of the invention to provide a surgical handpiece, as aforesaid, wherein the passageway extends centrally through the driven shaft and is connectable through a sealed connection to a central passageway in a tool connected thereto and having an implement rotary driven by the driven shaft of the motor.

It is a further object of the invention to provide a surgical handpiece, as aforesaid, wherein one end of the driven shaft includes a tool chucking means adapted to effect a rotary driving of the implement in a tool connected therewith.

It is a further object of the invention to provide a surgical handpiece, as aforesaid, wherein the tool chucking means includes a quick connect and a quick release mechanism for quickly coupling and decoupling the tool from the driven shaft.

It is a further object of the invention to provide a surgical handpiece, as aforesaid, wherein the suction control mechanism includes a valve body internally of the surgical handpiece housing and controllable between open and closed positions by a control member mounted externally of the surgical handpiece housing and operable by one or more digits of the user's hand holding the surgical handpiece.

It is a further object of the invention to provide a surgical handpiece, as aforesaid, wherein the surgical handpiece housing includes a yieldable stop mechanism for holding the tool in the housing while decoupled from the driven shaft so that the handpiece can be conveniently manipulated with the decoupled tool therein to facilitate removal and replacement with another tool.

It is a further object of the invention to provide a surgical handpiece, as aforesaid, which is easy to operate and is virtually free of maintenance.

SUMMARY OF THE INVENTION

The objects and purposes of the invention are met by providing a surgical handpiece having a housing with an interior cavity and an exterior surface adapted to be gripped by the hand of a user. A rotary drive mechanism is provided in the interior cavity of the housing, the rotary drive mechanism having a rotatably supported driven shaft with a passageway extending axially therethrough. The housing has a suction connection thereon and the housing has a suction control device operable between first and second operative positions and oriented in series intermediate the suction connection and a first end of the driven shaft for preventing suction from being applied to the passageway when in the first operative position and for connecting suction to the passageway when in the second operative position.

BRIEF DESCRIPTION OF THE DRAWINGS

Further objects and purposes of this invention will be apparent to persons acquainted with this field of technology and upon a reading of the following specification with reference to accompanying drawings, in which.

DETAILED DESCRIPTION

Figure 1:
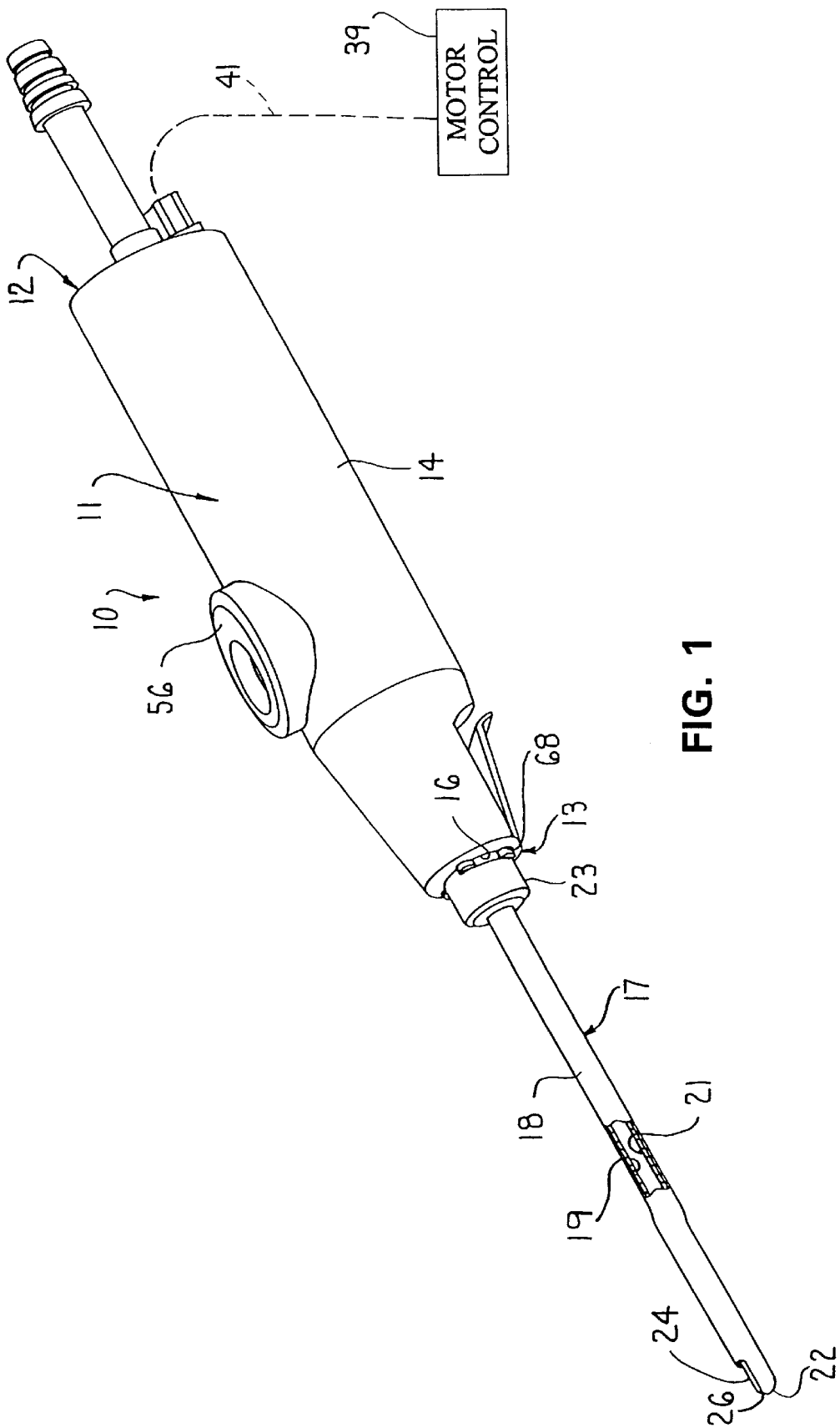
FIG. 1 is an isometric view of a surgical handpiece embodying the invention.

A surgical handpiece 10 embodying the invention is illustrated in the drawings and, as shown in FIG. 1, the handpiece includes an elongate housing 11 having a proximal end 12 and a distal end 13 and an exterior surface 14 adapted to be easily gripped by one hand of a user, usually the surgeon. The distal end 13 has a port 16 into which is received a surgical tool 17. The surgical tool 17 is of a conventional configuration having an outer hollow sheath 18 having therein a hollow rotatable shaft 19 with an elongate central passageway 21 extending from the distal end 22 of the tool through to the proximal end 23 thereof received in the port 16. The distal end of the shaft 19 has a cutting implement 24 exposed through an opening 26 in the sheath 18.

Figure 2:
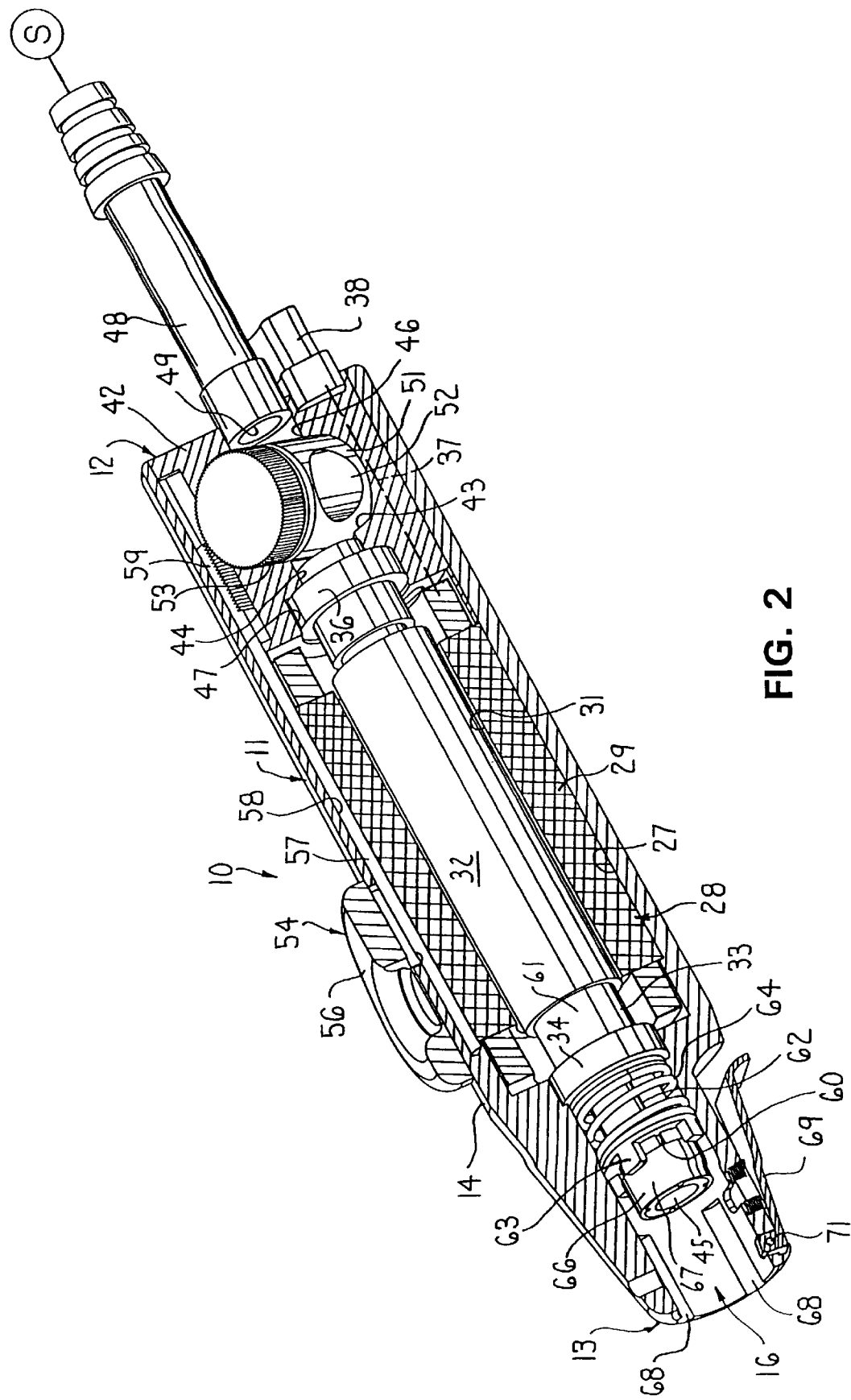
FIG. 2 is an isometric view similar to FIG. 1, except that a longitudinal section is shown.
Figure 3:
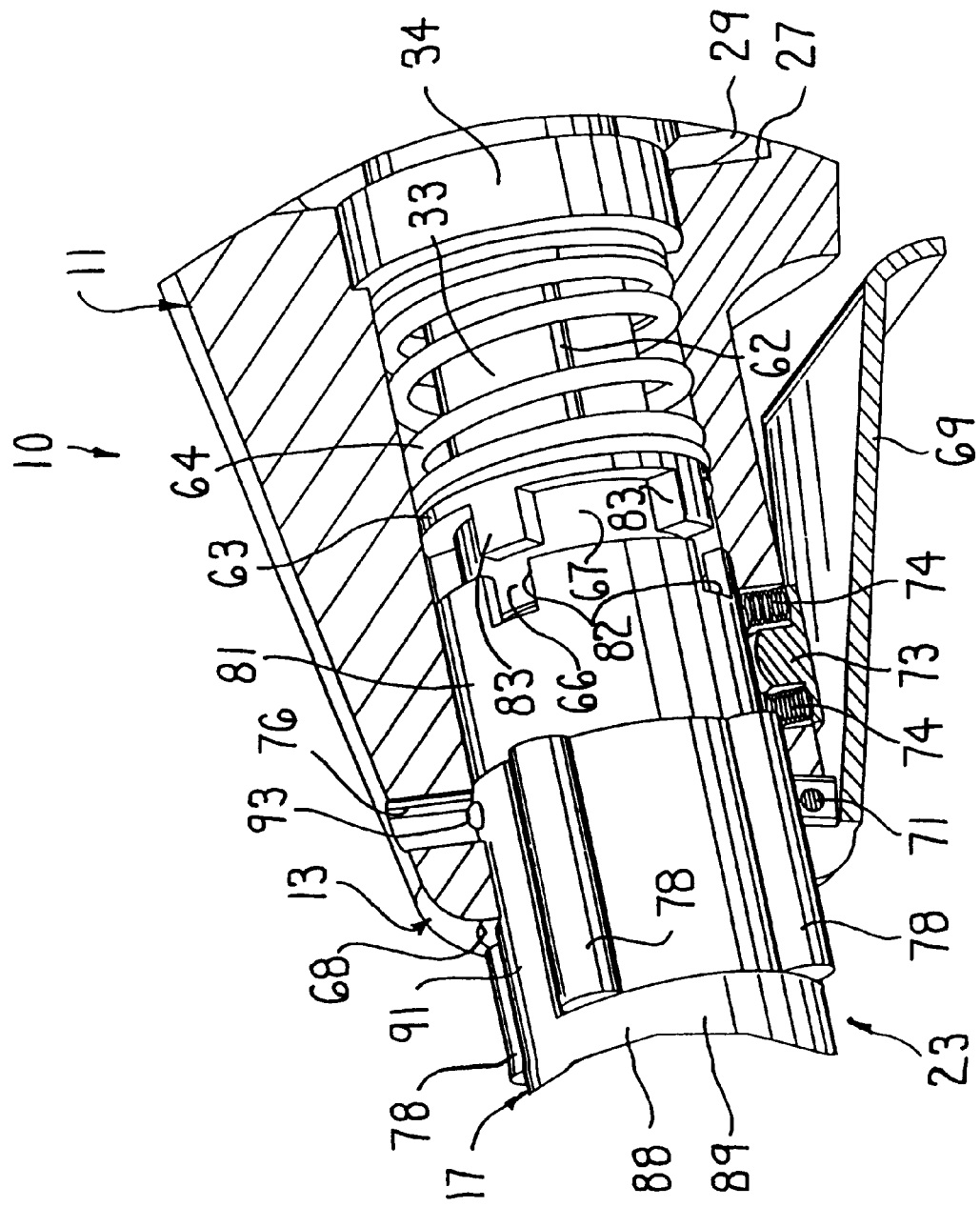
FIG. 3 is an enlarged fragment of the surgical handpiece housing with a tool being shown in the opening provided at the distal end of the housing decoupled from the driven shaft.

Referring now to FIG. 2, the housing 11 has an interior cavity 27 which opens axially outwardly at the proximal end 12 thereof. The port 16 at the distal end 13 is of a diameter smaller than the diameter of the cavity 27 and opens into the cavity 27. An electric motor 28 is provided in the cavity 27. More specifically, the electric motor 28 includes a conventional stator 29, shown only schematically, comprised of a plurality of windings (not shown in detail). The stator 29 has a central passageway 31 therethrough and in which is provided a rotor 32. The rotor 32 is provided on a hollow shaft 33 which is rotatably supported in the housing 11 by a pair of axially spaced bearings 34 and 36. Wiring schematically illustrated at 37 is electrically connected to and extends from the stator windings 29 to an electrical connector 38 oriented externally of and on the housing 11. A motor control circuit 39 (FIG. 1) is connected by an electrical cord 41 to the electrical connector 38 in a conventional manner. The motor control circuitry 39 is adapted to be controlled by the user (usually the surgeon) and, in this particular embodiment, by the user's foot.

In this particular embodiment, the housing 11 includes an end piece 42 received in the opening into the cavity 27 at the proximal end 12 of the housing 11. The end piece includes a central chamber 43 and a pair of axially aligned ports 44 and 46 opening into the chamber 43. In this particular embodiment, the axially aligned ports 44 and 46 are also axially aligned with the axis of the hollow interior 45 of the shaft 33. In fact, the hollow shaft 33 terminates in the port 44 and the bearing 36 is mounted in a channel 47 provided therefor in the distal end of the end piece 42. The port 46 has received therein a connection member 48 with a central passageway 49 extending therethrough. The connection member 48 is adapted to be connected to a suction source S.

Figure 10:
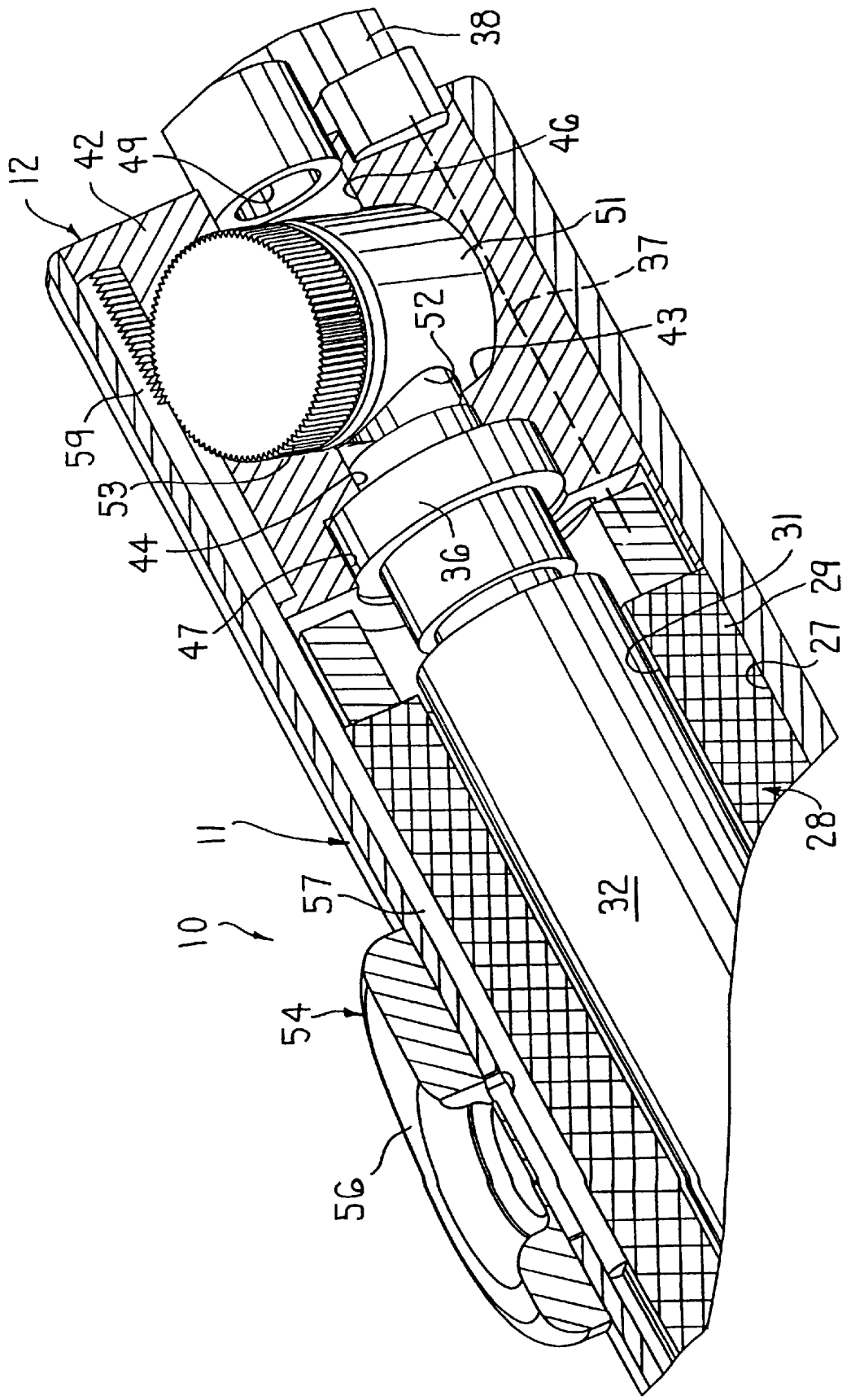
FIG. 10 is an isometric view of the proximal end of the surgical handpiece.

The chamber 43 is, in this particular embodiment, cylindrical with the axis of the cylinder intersecting and extending perpendicular to the axes of the axially aligned ports 44 and 46. A cylindrical valve member 51 is received in the chamber 43 and is adapted to rotate about its axis and the axis of the cylindrical chamber 43. The valve member 51 has a central opening 52 therethrough which, upon rotary movement of the valve member 51, is adapted to become axially aligned with the axially aligned ports 44 and 46, when in a first position thereof (FIG. 10) and out of axially alignment with the ports 44 and 46, when in a second position thereof (FIG. 2). The valve member 51 includes a plurality of gear teeth 53 oriented on the cylindrical surface thereof and adjacent one end thereof.

The position of the valve member 51 is controlled by a valve positioning device 54 slidably mounted on the exterior surface 14 of the housing 11. The valve positioning device includes a button 56 adapted to be engaged by a digit of the user's hand and slid lengthwise of the housing 11 in a known manner. The button 56 has attached thereto an elongated rod 57 oriented in a passageway 58 therefor inside the housing 11. The end of the rod 57 adjacent the proximal end 12 has a gear rack 59, the teeth of which engage the teeth 53 on the valve member 51. As a result of a back and forth sliding of the button 56 and connected rod 57, the operatively engaged teeth 53 and 59 will effect a rotation of the valve member 51 to and between its respective first and second positions described above.

The distal end of the driven shaft 33, that is, the end remote from the valve member 51, terminates in the aforementioned port 16. The peripheral surface 61 of the shaft 33 has a plurality of circumferentially spaced and axially extending grooves 62 therein. A coupling ring 63 has a plurality of radially inwardly extending prongs 60 received in the aforementioned grooves 62 to facilitate a guided axial movement of the coupling ring 63 toward and away from the bearing 34. The prongs 60 also assure that the coupling ring 63 will be rotatably driven with the shaft 33. A spring 64 is interposed between the coupling ring 63 and a spring abutment ring 65 (FIGS. 6 and 7) adjacent the bearing 34 to continually urge the coupling ring 63 toward an end stop defined by a sleeve 66 also having a plurality of radially inwardly extending splines received in the grooves 62 so as to guide the sleeve 66 during assembly onto the distal end of the driven shaft 33. The sleeve 66 has a smooth, radially outwardly facing surface 67 thereon.

The entry region from the distal end 13 of the housing 11 into the port 16 is provided with a plurality of axially extending guide grooves 68. Additionally, there is also provided a lever arm 69 pivotally secured to the exterior part of the housing 11 as by a shaft 71 to the distal end 13 of the housing 11. Adjacent the lever arm 69 there is provided an opening 72 through the wall of the distal end 13 of the housing 11 and in which is provided a reciprocally movable T-shaped button 73 and a plurality of small compression springs 74 oriented between the housing and the flanges of the T for continually urging the T-shaped button 73 away from the interior of the port 16 and into engagement with the lever arm 69. A further opening 76 is provided through the wall of the housing 11 adjacent the distal end 13 on a side of the port diametrically opposed to the opening 72.

Figure 4:
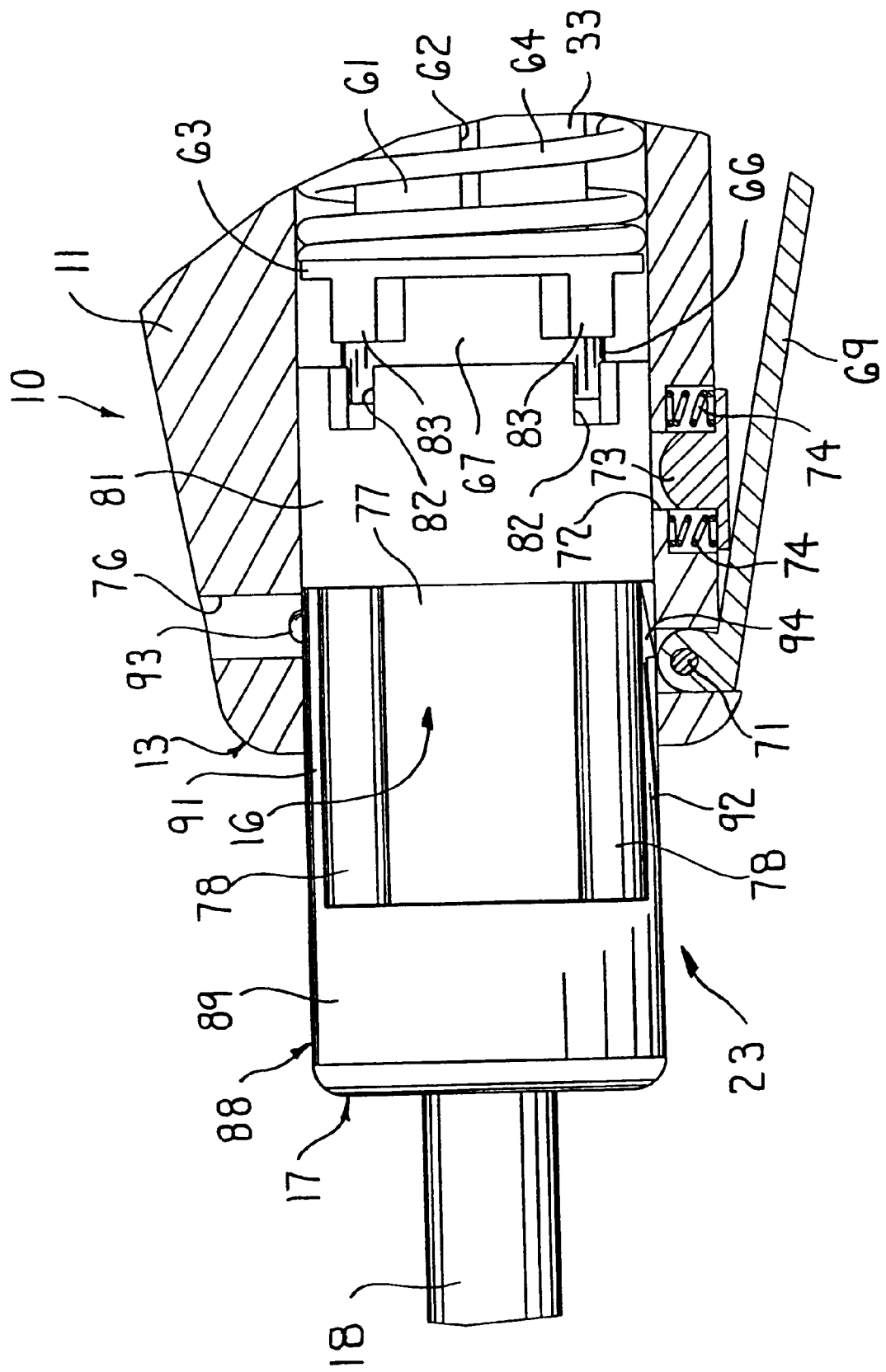
FIG. 4 is a side view of FIG. 3.
Figure 5:
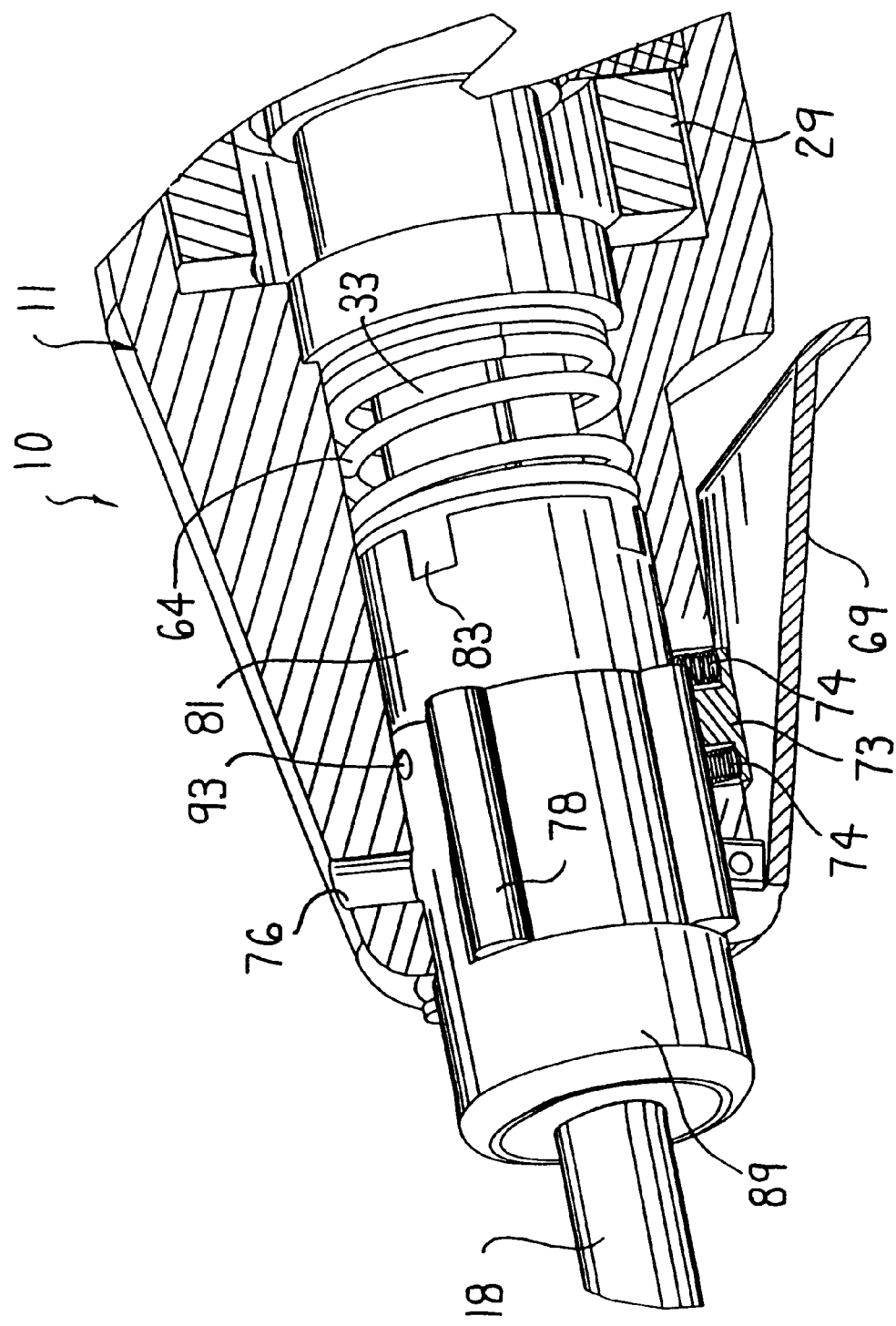
FIG. 5 is an enlarged isometric view of the surgical handpiece with the tool drivingly coupled to the driven shaft.
Figure 6:
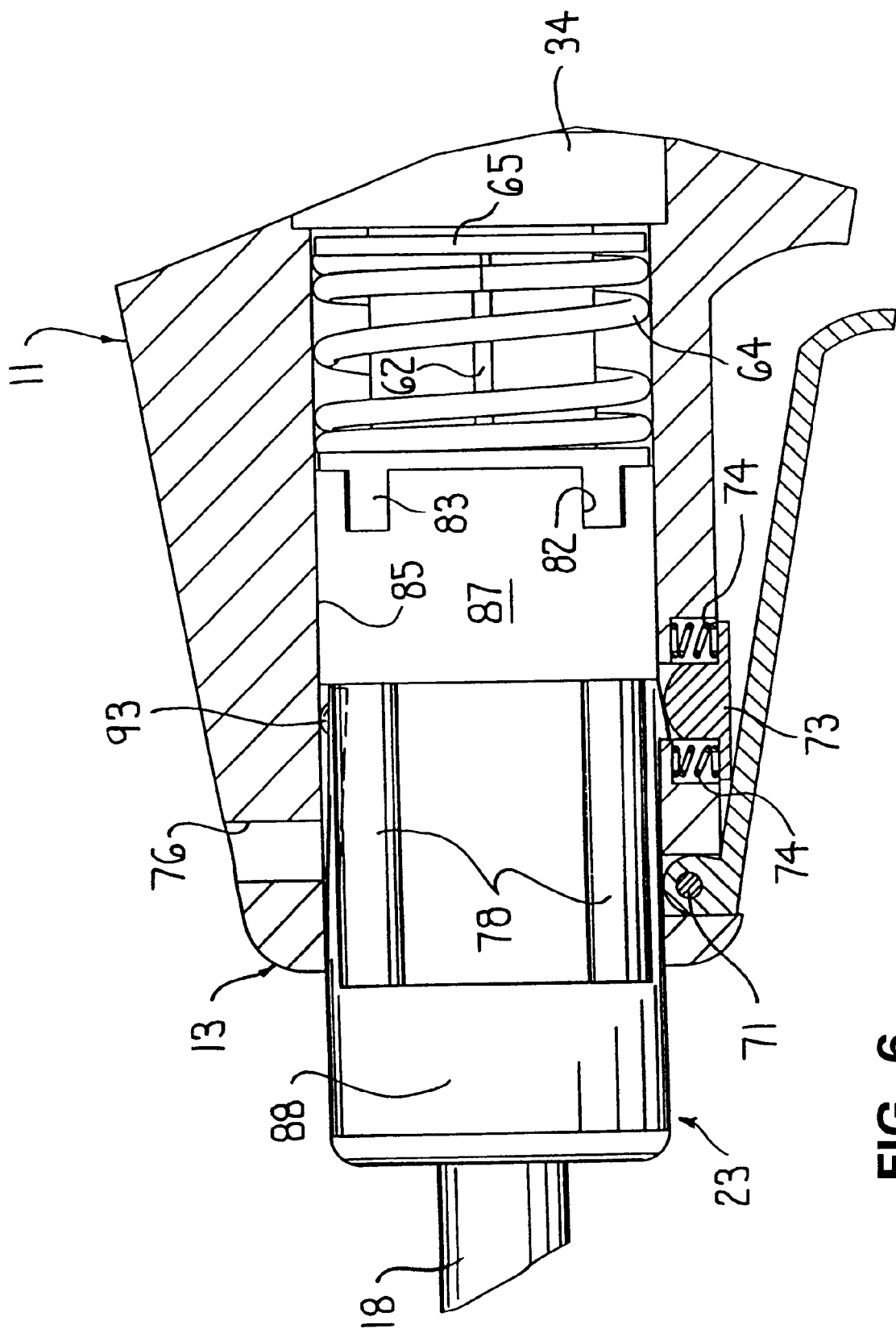
FIG. 6 is a side view of FIG. 5.
Figure 7:
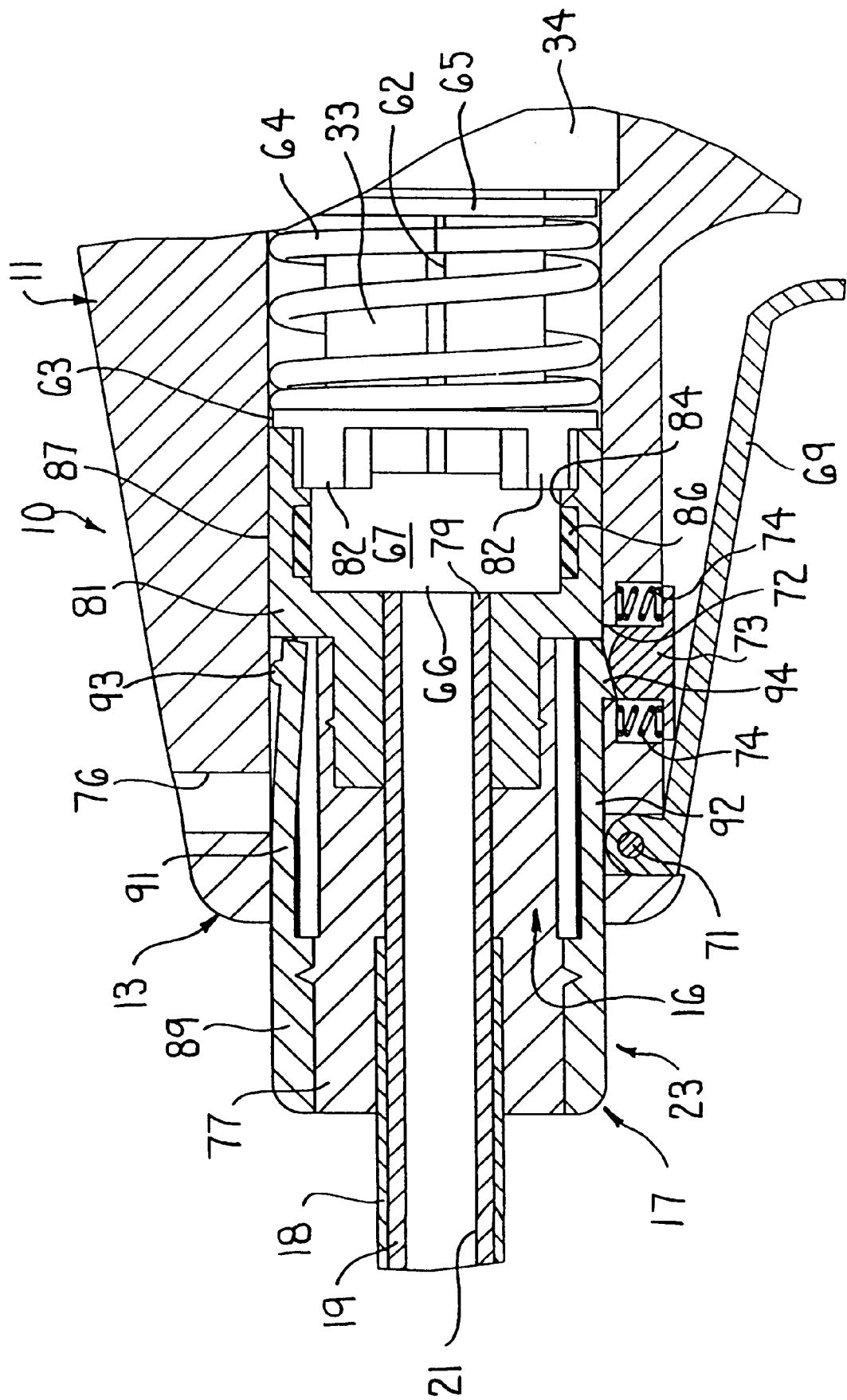
FIG. 7 is a central sectional view of the structure illustrated in FIG. 6.

The proximal end 23 of the tool 17 is shown in FIGS. 3–9 in various stages of being inserted into the port 16 into the housing 11 as well as released therefrom. The proximal end of the tool includes an enlarged sleeve 77 fixedly secured to the sheath 18 and having a plurality of radially outwardly extending enlargements 78 thereon guidingly received in the guide grooves 68 inside the port 16. The rotatable shaft 19 of the tool 17 extends through the interior of the sleeve 77 and has on the proximal end 79 thereof a coupling element 81. The coupling element 81 and the shaft 19 are drivingly coupled to one another and are adapted to rotate relative to the sleeve 77. The coupling member 81 has a plurality of circumferentially spaced recesses 82 into each of which is received a tooth 83 on the coupling ring 63. The proximal end of the coupling element 81 has an enlarged opening 84, the diameter of which is configured to slidingly engage the exterior surface 67 of the sleeve 66. A compressible seal member 86 is provided on the inside facing surface of the opening 84 and is adapted to be compressed into engagement with the surface 67 of the sleeve 66 when the coupling element 81 is slid axially to the right onto the sleeve 66 so that the teeth 83 on the coupling ring 63 will be received in the recesses 82 on the coupling element 81 as shown in FIGS. 5–7. An exterior surface 87 of the coupling element 81 is spaced a nominal clearance from the interior surface 85 of the port 16 so as to facilitate a friction-free rotation of the coupling element 81 therein. The same is true between the coupling element 81 and the sleeve 77.

A fastener element 88 is provided for locking the proximal end 23 of the tool 17 into the distal end 13 of the housing 11. The fastener element 88 includes a sleeve-like portion 89 sleeved over the outside of the sleeve 77 and has a pair of diametrically spaced and axially extending arms 91 and 92 extending to the right therefrom as best illustrated in FIG. 7. Each of the arms 91 and 92 is elastically yieldable. The arm 91 has an upstanding bead 93 adjacent the free end thereof and the arm 92 has an upstanding barb 94 adjacent the free end thereof. The fastener element 88 is fixed to the sleeve 77 and the arms 91 and 92 are configured to flex between the positions illustrated in FIGS. 4 and 7.

OPERATION

While the operation of the surgical handpiece 10 described above will be apparent to persons of ordinary skill in the art, the following operational sequence is provided for convenience purposes only.

When it is desired to insert a tool 17 into the port 16 at the distal end 13 of the housing 11, the coupling element 81 is axially aligned with the axis of the port 16 and moved to the right thereinto. The enlargements 78 are each to be aligned with the respective guide groove 68 so that a guiding movement of the sleeve 77 will occur. The bead 93 will first be received in the opening 76 while the barb 94 is flexed radially inwardly to the position illustrated in FIG. 4. In this position, the teeth 83 on the coupling ring 63 will be spaced from the recesses 82 in the coupling element 81 as illustrated in FIG. 4. The user need only urge the tool 17 to the right so that the bead 93 will be urged radially inwardly and slide along the interior facing surface 85 of the port 16 until the teeth 83 are received in the recesses 82 as illustrated in FIGS. 5–7. In this position, the barb 94 will spring radially outwardly into the opening 72. During this insertion movement, the spring 64 is compressed and, as a result, the axially directed return force of the spring 64 will urge the barb 94 into the wall surface of the opening 72. Thus, the tool 17 is now locked into the port 16 at the distal end 13 of the housing 11 and drivingly coupled to the driven shaft 33.

Since the tool 17 is now drivingly coupled to the driven shaft 33 by reason of the teeth 83 on the coupling ring 63 being drivingly received in the recesses 82 in the coupling element 81, the drive motor 28 can now be energized by activation of the motor control circuitry 39. A rotational driving of the shaft 19 of the tool will effect an operation of the cutting element 24 at the distal end 22 of the tool 17 to remove the material being operated on. When the surgical area is flushed with a saline solution, the detritus material and the saline solution can be removed from the surgical site by operation of the button 56 on the exterior surface 14 of the housing 11 to effect a movement of the valve member 51 from the position illustrated in FIG. 2 to the position illustrated in FIG. 10, or positions in between fully closed (FIG. 2) and fully opened (FIG. 10), so that suction will be selectively applied to the passageway 45 through the central portion of the driven shaft 33 and to the axially aligned passageway 21 in the tool 17 to allow the detritus material and saline solution to be drawn from the surgical site through the central region of the surgical handpiece 10 out through the passageway 49 through the connection member 48. When suction is no longer required at the surgical site, the button 56 is moved in the opposite direction to return the valve from the position illustrated in FIG. 10 to the position illustrated in FIG. 2.

Figure 8:
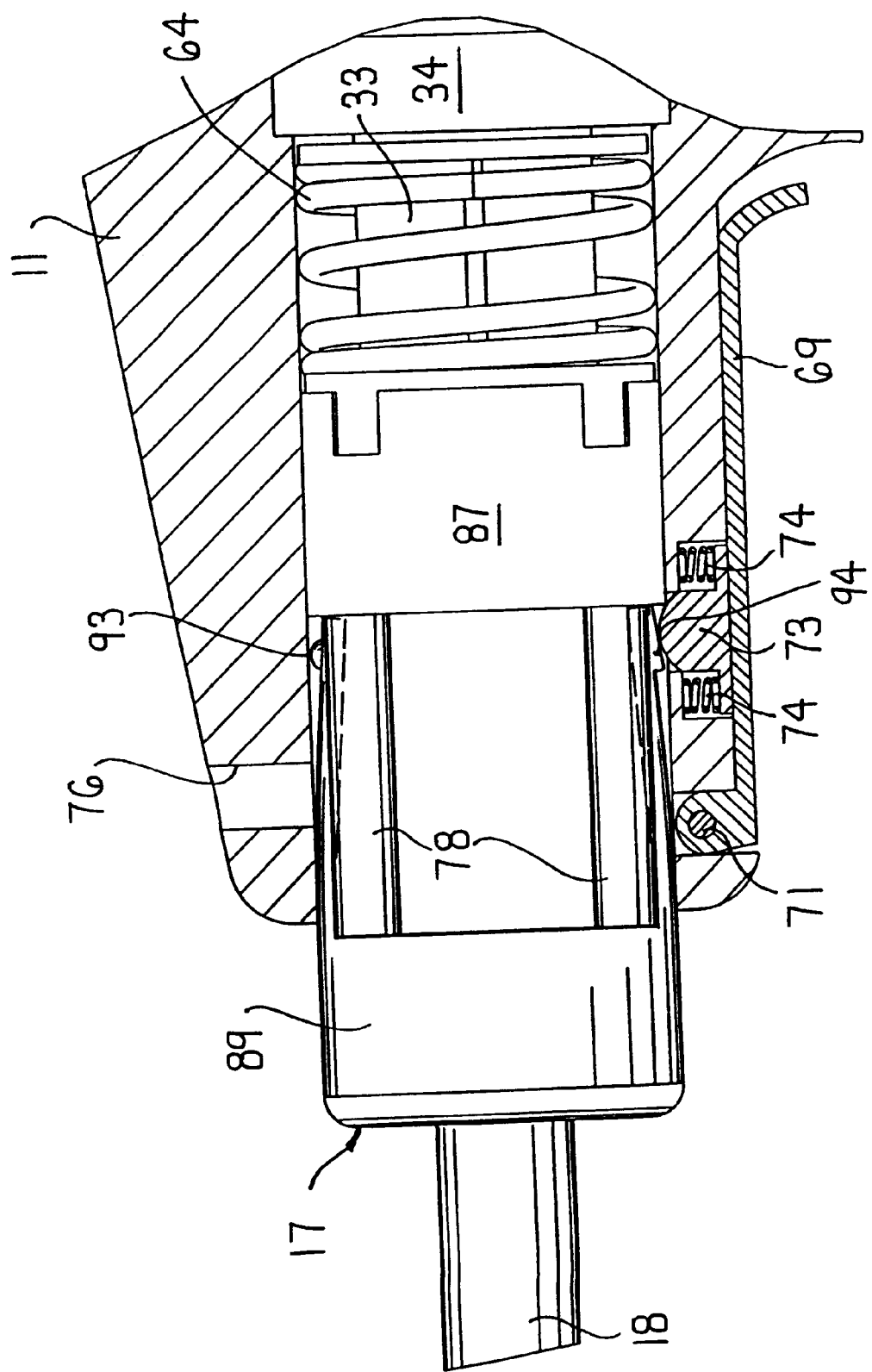
FIG. 8 is a side view similar to FIG. 6 but with the release lever activated to release the tool.
Figure 9:
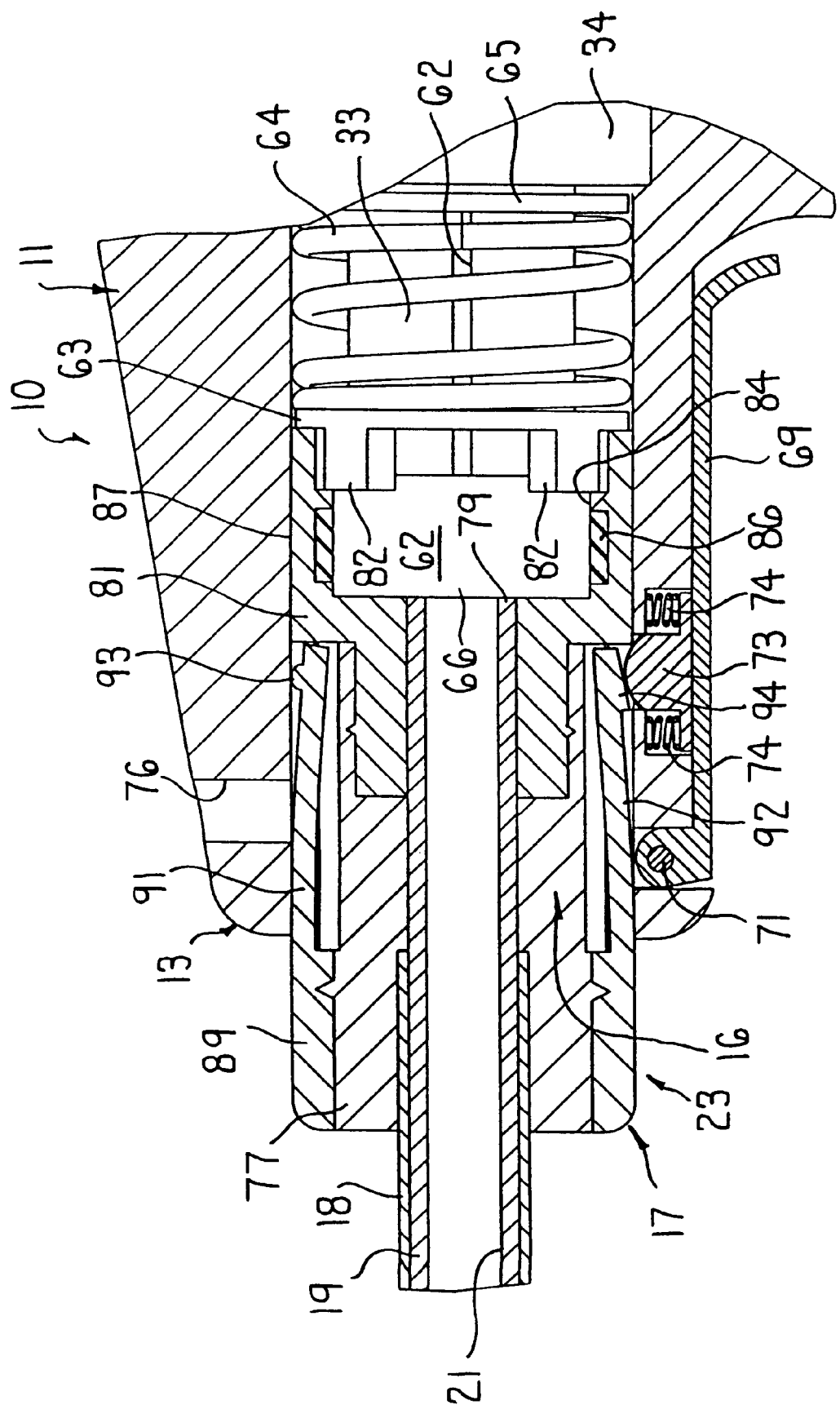
FIG. 9 is a central sectional view of FIG. 8.

When it is desired to remove the tool 17 from its operative coupling to the housing 11 and driven shaft 33, the lever arm 69 is pivotally moved about the axis of the shaft 71 from the FIG. 7 position to the FIG. 8 position so as to cause the lever arm 69 to engage the T-shaped button 73 to urge same into the opening 72 and effect a compression of the compression springs 74. During the aforesaid movement, the T-shaped button 73 will engage the barb 94 and urge it radially inwardly as shown in FIGS. 8 and 9. The spring return force of the yet compressed spring 64 will urge the proximal end 23 of the tool 17 to the left with sufficient force to eject the tool from engagement with the teeth on the coupling ring 63. The tool 17 would otherwise shoot outwardly from the distal end 13 of the housing 11 were it not for the bead 93 being received in the opening 76 as illustrated in FIG. 4. The bead 93 will prevent the tool from being shot out from the port 16. The user will need only grasp the tool and forcibly pull it from the port 16, such movement causing the bead 93 and the arm 91 on which it is mounted to yield to enable such removal of the tool from the port 16.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A powered surgical handpiece for actuating a cutting attachment having an outer hub, an inner hub and a rotatable inner tube that is connected to the inner hub, said handpiece comprising:

a housing having a proximal end with a proximal end port and a distal end with a distal end port, the distal end port being axially aligned with the proximal end port;

a stator fixedly mounted in said housing, said stator having a passageway located between the proximal end and the distal end of the housing;

a rotor disposed in the passageway of said stator so as to form a motor with said stator, said rotor having a hollow shaft that is rotatably mounted to said housing, said shaft having a longitudinal axis that is axially aligned with the proximal end port of said housing, a head end located in said distal end port of said housing, the head end being sleeve-shaped, and an open proximal end in fluid communication with the proximal end port; and a suction fitting attached to the proximal end port of said handpiece through which a suction is drawn through said rotor shaft;

a coupling member movably mounted to the distal end of said housing for releasably holding the outer hub of the cutting attachment in a static position in the distal end port; and an inner hub coupling assembly for releasably holding the inner hub of the cutting attachment to said rotor shaft so that the inner hub and inner tube rotate in unison with said shaft, said inner hub coupling assembly including:

a coupling ring that is disposed over said rotor shaft that has at least one tooth for engaging a complementary notch formed in the inner hub and that is fitted to said shaft to rotate in unison with said shaft and to move longitudinally relative to the head end of said shaft; and a biasing member that extends between said handpiece housing and said coupling ring for urging said coupling ring towards said inner hub so that said at least one tooth is urged into the complementary notch formed in said inner hub.

2. The surgical handpiece of claim 1, wherein: said coupling ring is formed with a plurality of teeth.

3. The surgical handpiece of claim 1, wherein:

said rotor shaft is formed so as to have at least one longitudinally extending groove on an outer surface thereof, the at least one groove being located between said stator and the head end of said shaft; and said coupling ring is formed with a prong that is seated in the at least one groove.

4. The surgical handpiece of claim 1, wherein said biasing member is a spring.

5. The surgical handpiece of claim 1, wherein:
said handpiece housing is provided with a chamber through which there is fluid communication from a proximal end opening in said shaft to the proximal end port of said housing; and
a valve is disposed in the chamber for regulating fluid flow from said shaft through the proximal end port of said housing.

6. A powered surgical handpiece for actuating a cutting attachment having an outer hub, an inner hub that is rotatable relative to said outer hub and inner tube that is connected to the inner hub to rotate in unison with said inner hub, said handpiece including:
a housing, said housing having a proximal end with a proximal end opening, a distal end with a distal end opening, the distal end opening being axially aligned with the proximal end opening and a suction fitting attached to the proximal end opening through which a suction is drawn; and
a motor, said motor including: a stator that is fixedly mounted in said housing; and a rotor that is disposed in said stator, said rotor having a hollow shaft that is rotatably mounted in said housing that extends from the proximal end of said housing to the distal end of said housing through which fluid flows between the openings of said housing, said shaft being longitudinally axially aligned with the proximal end opening of said housing and having a head end that is located in the distal end of said housing;
an outer hub coupling assembly attached to the distal end of said housing for releasably holding the outer hub of the cutting attachment in a static position in the distal end opening of said housing, said outer hub coupling assembly including a manually actuated release lever for releasing the outer hub from said housing; and
an inner hub coupling assembly for releasably holding the inner hub of the cutting attachment to said rotor shaft so that the inner hub and inner tube rotate in unison with said shaft, said inner hub coupling assembly including:
a coupling ring that is disposed over said rotor shaft that has at least one tooth for engaging a complementary notch formed in the inner hub and that is fitted to said shaft to rotate in unison with said shaft and to move longitudinally relative to the head end of said shaft; and
a spring that extends between said handpiece housing and said coupling ring for urging said coupling ring towards said inner hub so that said at least one tooth is urged into the complementary notch formed in said inner hub.

7. The surgical handpiece of claim 6, wherein:
said handpiece housing is provided with a chamber through which there is fluid communication from a proximal end opening in said shaft to the proximal end port of said housing; and
a valve is disposed in the chamber for regulating fluid flow from said shaft through the proximal end port of said housing.

8. A powered surgical handpiece for actuating a cutting attachment having an outer hub, an inner hub and a rotatable inner tube that is connected to the inner hub, said handpiece comprising:
a housing having a proximal end with a proximal end port and a distal end with a distal end port, the distal end port being axially aligned with the proximal end port;
a stator fixedly mounted in said housing, said stator having a passageway located between the proximal end and the distal end of the housing;
a rotor disposed in the passageway of said stator so as to form a motor with said stator, said rotor having a hollow shaft that is rotatably mounted to said housing, said shaft having a longitudinal axis that is axially aligned with the proximal end port, a head end located in the distal end, the head end being sleeve-shaped and having an outer surface and extending to the distal end of said housing so that fluid can flow through said shaft from the distal end port to the proximal end port;
a suction fitting attached to the proximal end port of said handpiece through which a suction is drawn through said shaft;
a first coupling member movably mounted to the distal end of said housing for releasably holding the outer hub of the cutting attachment in a static position in said distal end port; and
a second coupling member mounted to said rotor for releasably coupling the inner hub of the cutting attachment to said shaft so that the inner hub and inner tube rotate in unison with the shaft,
wherein;
said housing is formed with a chamber in the proximal end through which there is fluid communication from a proximal end opening of said shaft to the proximal end port of said housing;
a valve member is disposed in the chamber for regulating fluid flow through the proximal end port of said housing; and
a button is movably mounted to an outer surface of said housing adjacent the distal end of said housing and said button is attached to said valve member for controlling an open/closed state of said valve member.

9. The surgical handpiece of claim 8, wherein a control rod is movably disposed in said housing and extends from said button to said valve member, wherein said control rod opens/closes said valve member in response to displacement of said button.

10. A powered surgical handpiece for actuating a cutting attachment having an outer hub, an inner hub and a rotatable inner tube that is connected to the inner hub, said handpiece comprising:
a housing, said housing have a proximal end with a proximal end opening, a distal end with a distal end opening, the distal end opening being axially aligned with the proximal end opening, a chamber in the proximal end of said housing, the chamber being in fluid communication with the proximal end opening and a suction fitting attached to the proximal end opening through which a suction is drawn; and
a valve member disposed in the chamber in the housing for regulating fluid flow through the proximal end opening and a valve button mounted to an outer surface of said housing adjacent the distal end of the housing, said valve button being connected to said valve member for regulating an open/closed state of said valve member;
a motor, said motor including: a stator that is fixedly mounted in said housing; and a rotor that is disposed in said stator, said rotor having a hollow shaft that is rotatably mounted in said housing that extends from the chamber in said housing to the distal end opening of said housing, said shaft being longitudinally axially aligned with the proximal end opening of said housing and having a head end that is located in the distal end of said housing;

a first coupling assembly mounted to said handpiece housing for releasably locking the outer hub of the cutting attachment in a static position relative to said handpiece; and a second coupling assembly attached to said rotor shaft for releaseably holding the inner hub of the cutting attachment to said rotor shaft so that said inner hub and the inner tube rotate in unison with said rotor shaft.

11. The surgical handpiece of claim 10, wherein a control rod is movably disposed in said housing and extends from said button to said valve member, wherein said control rod opens/closes said valve member in response to displacement of said button.

* * * * *